US011590018B2

(12) United States Patent
Uridil et al.

(10) Patent No.: US 11,590,018 B2
(45) Date of Patent: Feb. 28, 2023

(54) FECAL MANAGEMENT APPLICATOR AND ASSEMBLY

(71) Applicant: Medline Industries, LP, Northfield, IL (US)

(72) Inventors: Morgan Uridil, Evanston, IL (US); Amanda Roszkowiak, Schaumburg, IL (US)

(73) Assignee: Medline Industries, LP, Northfield, IL (US)

( * ) Notice: Subject to any disclaimer, the term of this patent is extended or adjusted under 35 U.S.C. 154(b) by 894 days.

(21) Appl. No.: 16/411,380

(22) Filed: May 14, 2019

(65) Prior Publication Data

US 2020/0360173 A1    Nov. 19, 2020

(51) Int. Cl.
*A61F 5/451*    (2006.01)
*A61F 5/44*    (2006.01)
*A61F 2/00*    (2006.01)

(52) U.S. Cl.
CPC ............ *A61F 5/451* (2013.01); *A61F 5/4404* (2013.01); *A61F 2/0009* (2013.01)

(58) Field of Classification Search
CPC ....... A61F 5/451; A61F 5/4404; A61F 2/0009
See application file for complete search history.

(56) References Cited

U.S. PATENT DOCUMENTS

| | | |
|---|---|---|
| 1,965,653 A | 7/1934 | Kennedy |
| RE20,061 E | 8/1936 | Kirk |
| 2,122,234 A | 6/1938 | McAuliffe |
| 2,333,342 A | 11/1943 | Slocumb |
| 2,631,586 A | 3/1953 | Reilly |
| 2,641,254 A | 6/1953 | Brown |
| 2,690,181 A | 9/1954 | Boyer |
| 2,974,666 A | 3/1961 | Coumbis |
| 3,032,036 A | 5/1962 | Rader |
| 3,086,527 A | 4/1963 | Forrest |
| 3,459,175 A | 8/1969 | Miller |
| 3,522,807 A * | 8/1970 | Millenbach ............ A61F 5/451 604/355 |
| 3,625,793 A | 12/1971 | Sheridan |
| 3,866,601 A | 2/1975 | Russell |
| 3,896,816 A | 7/1975 | Mattler |
| 4,030,500 A | 6/1977 | Ronnquist |

(Continued)

FOREIGN PATENT DOCUMENTS

| | | |
|---|---|---|
| JP | 2001000536 | 1/2001 |
| WO | 2008048856 | 4/2008 |

*Primary Examiner* — Guy K Townsend
(74) *Attorney, Agent, or Firm* — Fitch, Even, Tabin & Flannery LLP

(57) ABSTRACT

A fecal management applicator, a fecal management assembly, and a fecal management method are described herein. A fecal management applicator may include a handle portion, and a head portion extending from the handle portion. The head portion may include an inner head wall portion that extends axially from the handle portion and an outer head wall portion that extends radially outwardly from the inner head wall portion and curves over the inner head wall portion. The fecal management applicator may define a channel that extends continuously through the handle portion and the head portion along an entire axial length of the fecal management applicator.

22 Claims, 7 Drawing Sheets

(56) References Cited

U.S. PATENT DOCUMENTS

| | | | |
|---|---|---|---|
| 4,182,332 A * | 1/1980 | Delaney | A61F 5/451 |
| | | | 604/328 |
| RE30,365 E | 8/1980 | Mattler | |
| 4,333,460 A | 6/1982 | Miller | |
| 4,368,733 A * | 1/1983 | Sanidas | A61G 9/00 |
| | | | 604/327 |
| 4,445,898 A * | 5/1984 | Jensen | A61F 5/441 |
| | | | 604/338 |
| 4,471,782 A | 9/1984 | Shuffield | |
| 4,496,356 A | 1/1985 | Lognion | |
| 4,534,768 A | 8/1985 | Osburn | |
| D294,063 S | 2/1988 | Smith | |
| 4,752,288 A | 6/1988 | Hussey | |
| 4,772,260 A * | 9/1988 | Heyden | A61M 25/04 |
| | | | 604/269 |
| 4,784,656 A * | 11/1988 | Christian | A61F 5/441 |
| | | | 604/355 |
| D299,271 S | 1/1989 | Christensen | |
| D320,275 S | 9/1991 | Wada | |
| D330,764 S | 11/1992 | Lorentzon | |
| D344,133 S | 2/1994 | Stamler | |
| D345,016 S | 3/1994 | Stamler | |
| 5,312,384 A * | 5/1994 | Temple | A61F 5/44 |
| | | | 604/355 |
| D366,113 S | 1/1996 | Morgan | |
| 5,509,893 A | 4/1996 | Pracas | |
| 5,520,669 A * | 5/1996 | Mulholland | A61F 5/451 |
| | | | 604/328 |
| D377,216 S | 1/1997 | Mark | |
| 5,593,397 A * | 1/1997 | La Gro | A61F 5/443 |
| | | | 604/355 |
| D377,716 S | 2/1997 | Karon | |
| 5,714,225 A | 2/1998 | Hansen | |
| 5,741,239 A * | 4/1998 | Mulholland | A61F 5/451 |
| | | | 604/355 |
| 5,827,247 A | 10/1998 | Kay | |
| D402,199 S | 12/1998 | Saunders | |
| D428,142 S | 7/2000 | Stromblad | |
| 6,110,150 A | 8/2000 | Singo | |
| D430,703 S | 9/2000 | Leslie | |
| D431,093 S | 9/2000 | Leslie | |
| D432,714 S | 10/2000 | Leslie | |
| D434,525 S | 11/2000 | Angeletta | |
| D441,073 S | 4/2001 | Mark | |
| D450,153 S | 11/2001 | Knieriemen | |
| D450,836 S | 11/2001 | Mark | |
| D457,627 S | 5/2002 | Lamb | |
| D462,257 S | 9/2002 | Alexander | |
| D474,271 S | 5/2003 | Iori | |
| D474,689 S | 5/2003 | Dinsky | |
| 6,685,687 B2 * | 2/2004 | Mishima | A61F 13/495 |
| | | | 604/385.19 |
| 6,695,763 B2 | 2/2004 | Zunker | |
| D497,669 S | 10/2004 | Blanco | |
| 6,802,808 B2 | 10/2004 | Brady | |
| 6,916,312 B2 * | 7/2005 | Kondo | A61F 5/443 |
| | | | 604/277 |
| D518,177 S | 3/2006 | Blanco | |
| D519,635 S | 4/2006 | Hudak | |
| 7,101,357 B2 * | 9/2006 | Tanaka | A61F 5/443 |
| | | | 604/338 |
| D529,603 S | 10/2006 | Knickerbocker | |
| D532,109 S | 11/2006 | Carroll | |
| D540,469 S | 4/2007 | Grabinsky | |
| D542,916 S | 5/2007 | Squires | |
| D565,732 S | 4/2008 | Pech | |
| D566,270 S | 4/2008 | Strom | |
| D582,449 S | 12/2008 | Yamaguchi | |
| D589,612 S | 3/2009 | Sudo | |
| D598,093 S | 8/2009 | Kawamura | |
| D613,452 S | 4/2010 | Angeletta | |
| D615,651 S | 5/2010 | Hoffmann | |
| D619,715 S | 7/2010 | Kim | |
| D621,039 S | 8/2010 | Maxa | |
| D621,930 S | 8/2010 | Maxa | |
| D627,459 S | 11/2010 | Uchida | |
| D638,986 S | 5/2011 | Limongi | |
| D638,988 S | 5/2011 | Limongi | |
| D638,989 S | 5/2011 | Limongi | |
| D638,990 S | 5/2011 | Limongi | |
| D638,991 S | 5/2011 | Limongi | |
| D640,001 S | 6/2011 | Limongi | |
| D641,469 S | 7/2011 | Ruiz, Sr | |
| D650,089 S | 12/2011 | Kleyman | |
| D651,339 S | 12/2011 | Kirk, III | |
| D656,233 S | 3/2012 | Fischvogt | |
| D658,076 S | 4/2012 | McCoy | |
| D659,846 S | 5/2012 | Pearson | |
| D665,127 S | 8/2012 | Limongi | |
| D667,166 S | 9/2012 | Strube | |
| D667,954 S | 9/2012 | Mastri | |
| 8,277,427 B2 * | 10/2012 | Edvardsen | A61F 5/443 |
| | | | 604/355 |
| D674,487 S | 1/2013 | Kile | |
| D678,522 S | 3/2013 | Gustavsson | |
| D678,783 S | 3/2013 | Wilcox | |
| D687,143 S | 7/2013 | Ogura | |
| 8,480,640 B2 * | 7/2013 | Santimaw | A61F 5/451 |
| | | | 604/332 |
| D691,262 S | 10/2013 | Shalon | |
| 8,574,206 B2 * | 11/2013 | Bjerregaard | A61F 5/442 |
| | | | 604/328 |
| D695,403 S | 12/2013 | Shalon | |
| 8,672,908 B2 * | 3/2014 | Todd | A61F 5/445 |
| | | | 604/338 |
| D709,188 S | 7/2014 | Guala | |
| D713,538 S | 9/2014 | Van Valen | |
| 8,840,594 B2 | 9/2014 | Sharma | |
| D715,495 S | 10/2014 | Yiu | |
| D720,452 S | 12/2014 | Jordan | |
| D724,731 S | 3/2015 | Shalon | |
| D726,956 S | 4/2015 | Ettlin | |
| D726,957 S | 4/2015 | Ettlin | |
| D727,614 S | 4/2015 | Griffith | |
| D729,446 S | 5/2015 | Babel | |
| D734,456 S | 7/2015 | Cromett | |
| D734,540 S | 7/2015 | Ettlin | |
| D738,265 S | 9/2015 | McNeeley | |
| D738,495 S | 9/2015 | Strong | |
| D744,098 S | 11/2015 | Suval | |
| D750,228 S | 2/2016 | Strong | |
| D752,287 S | 3/2016 | Bansal | |
| D753,825 S | 4/2016 | Shalon | |
| D754,343 S | 4/2016 | Shalon | |
| D757,937 S | 5/2016 | Tsai | |
| D767,132 S | 9/2016 | Shalon | |
| 9,452,080 B2 | 9/2016 | Holzbauer | |
| 9,463,110 B2 * | 10/2016 | Nishtala | A61F 5/44 |
| D772,400 S | 11/2016 | Sawicki | |
| D772,407 S | 11/2016 | Zhang | |
| D775,416 S | 12/2016 | Celia, Jr. | |
| 9,526,878 B2 | 12/2016 | Kucklick | |
| D776,805 S | 1/2017 | Homsy | |
| D778,410 S | 2/2017 | Smith | |
| D781,477 S | 3/2017 | Mehta | |
| D796,034 S | 8/2017 | Gilbert | |
| D808,010 S | 1/2018 | Denzer | |
| D815,737 S | 4/2018 | Bergstrom | |
| D816,898 S | 5/2018 | Shavit | |
| 9,956,119 B2 | 5/2018 | Ingalls | |
| D821,580 S | 6/2018 | Elam | |
| 9,999,757 B2 | 6/2018 | Chiang | |
| 10,022,108 B2 * | 7/2018 | Ohler | A61F 5/443 |
| D831,207 S | 10/2018 | Shalon | |
| D835,784 S | 12/2018 | Orr | |
| 10,179,050 B2 | 1/2019 | Scrantz | |
| D842,991 S | 3/2019 | Cable, Jr. | |
| D848,000 S | 5/2019 | Stuppy | |
| D851,245 S | 6/2019 | Baxter | |
| D854,241 S | 7/2019 | Star | |
| 10,441,396 B2 | 10/2019 | Kunz | |
| 10,485,644 B2 | 11/2019 | Orr | |
| 10,518,022 B1 | 12/2019 | Walker | |

(56) References Cited

U.S. PATENT DOCUMENTS

| | | |
|---|---|---|
| D873,997 S | 1/2020 | Ljunglöf et al. |
| D881,392 S | 4/2020 | Pujara |
| D882,081 S | 4/2020 | Sun |
| D889,754 S | 7/2020 | Coffin |
| D889,961 S | 7/2020 | Swart |
| D890,925 S | 7/2020 | Doubet |
| D891,249 S | 7/2020 | Lee |
| D892,321 S | 8/2020 | Newton |
| D892,400 S | 8/2020 | Nelson |
| D899,591 S | 10/2020 | Bergström |
| D899,680 S | 10/2020 | Jung |
| D899,681 S | 10/2020 | Jung |
| D900,302 S | 10/2020 | Ancerewicz |
| D900,997 S | 11/2020 | Ancerewicz |
| 10,898,701 B2 | 1/2021 | Boone |
| D915,591 S | 4/2021 | Cao |
| D925,733 S | 7/2021 | Doubet |
| D925,737 S | 7/2021 | Andersen |
| D926,320 S | 7/2021 | Sweeney |
| 11,103,377 B1 | 8/2021 | Weston |
| D930,184 S | 9/2021 | Johnson |
| 11,109,952 B2 | 9/2021 | Andersson |
| D939,696 S * | 12/2021 | Uridil .................. A61F 13/495 D24/119 |
| 11,311,406 B2 * | 4/2022 | Roszkowiak ......... A61F 5/4405 |
| 2002/0138058 A1 * | 9/2002 | Mishima ............... A61F 13/495 604/385.19 |
| 2003/0088217 A1 | 5/2003 | Bergeron |
| 2004/0122384 A1 * | 6/2004 | Evangelista ............ A61F 5/443 977/841 |
| 2005/0137526 A1 | 6/2005 | Machado |
| 2006/0195006 A1 | 8/2006 | Daurelle |
| 2007/0282241 A1 | 12/2007 | Squires |
| 2009/0062755 A1 | 3/2009 | Burgess |
| 2009/0093784 A1 * | 4/2009 | Hansen .................. A61F 5/443 604/385.05 |
| 2009/0171268 A1 | 7/2009 | Williams, Jr. |
| 2010/0234821 A1 * | 9/2010 | Bjerregaard ........ A61M 3/0287 604/328 |
| 2011/0282311 A1 * | 11/2011 | Nishtala .................. A61F 5/442 604/332 |
| 2012/0116336 A1 | 5/2012 | Sharma |
| 2013/0192594 A1 | 8/2013 | Addington |
| 2014/0018775 A1 | 1/2014 | Swords |
| 2014/0121596 A1 | 5/2014 | Bo |
| 2014/0296832 A1 | 10/2014 | Karmazyn |
| 2014/0323909 A1 * | 10/2014 | Kim ..................... A61B 5/4255 604/355 |
| 2015/0011955 A1 | 1/2015 | Sharma |
| 2015/0246212 A1 | 9/2015 | Burstein |
| 2016/0339166 A1 | 11/2016 | Adam |
| 2017/0312116 A1 | 11/2017 | Laniado |
| 2018/0043086 A1 | 2/2018 | Foley |
| 2018/0043087 A1 | 2/2018 | Foley |
| 2019/0231969 A1 | 8/2019 | Hougaard |
| 2020/0078510 A1 | 3/2020 | Henry |
| 2020/0138618 A1 * | 5/2020 | Roszkowiak ........... A61F 5/441 |
| 2020/0138620 A1 | 5/2020 | Schwab |
| 2020/0188160 A1 | 6/2020 | Udayakumar |
| 2020/0215256 A1 | 7/2020 | Henry |
| 2020/0360173 A1 * | 11/2020 | Uridil .................. A61F 5/4404 |
| 2021/0015505 A1 | 1/2021 | Roszkowiak |
| 2021/0283325 A1 | 9/2021 | Henry |

\* cited by examiner

FECAL MANAGEMENT APPLICATOR AND ASSEMBLY

TECHNICAL FIELD

This disclosure relates generally to medical devices and, more particularly, to a fecal management applicator and a fecal management assembly.

BACKGROUND

Many challenges exist surrounding the care of patients that are incontinent, bedridden, or otherwise unable to care for themselves. Management of waste produced by such patients poses unique challenges. For example, the waste of a bedridden patient must be kept away from the patient for reasons of sanitation and the reduce the occurrence of sores and infection. Many fecal management systems include a collection bag. When the collection bag becomes full, the entire fecal management system must be removed from the patient. This may cause pain, discomfort, injury to the patient and can be inconvenient for the caregiver.

Described herein are fecal management devices and methods that seek to minimize, if not overcome, the disadvantages of the above-described fecal management systems.

DETAILED DESCRIPTION

Embodiments of the present disclosure are described herein. It is to be understood, however, that the disclosed embodiments are merely examples and other embodiments may take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures may be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Figure 1:
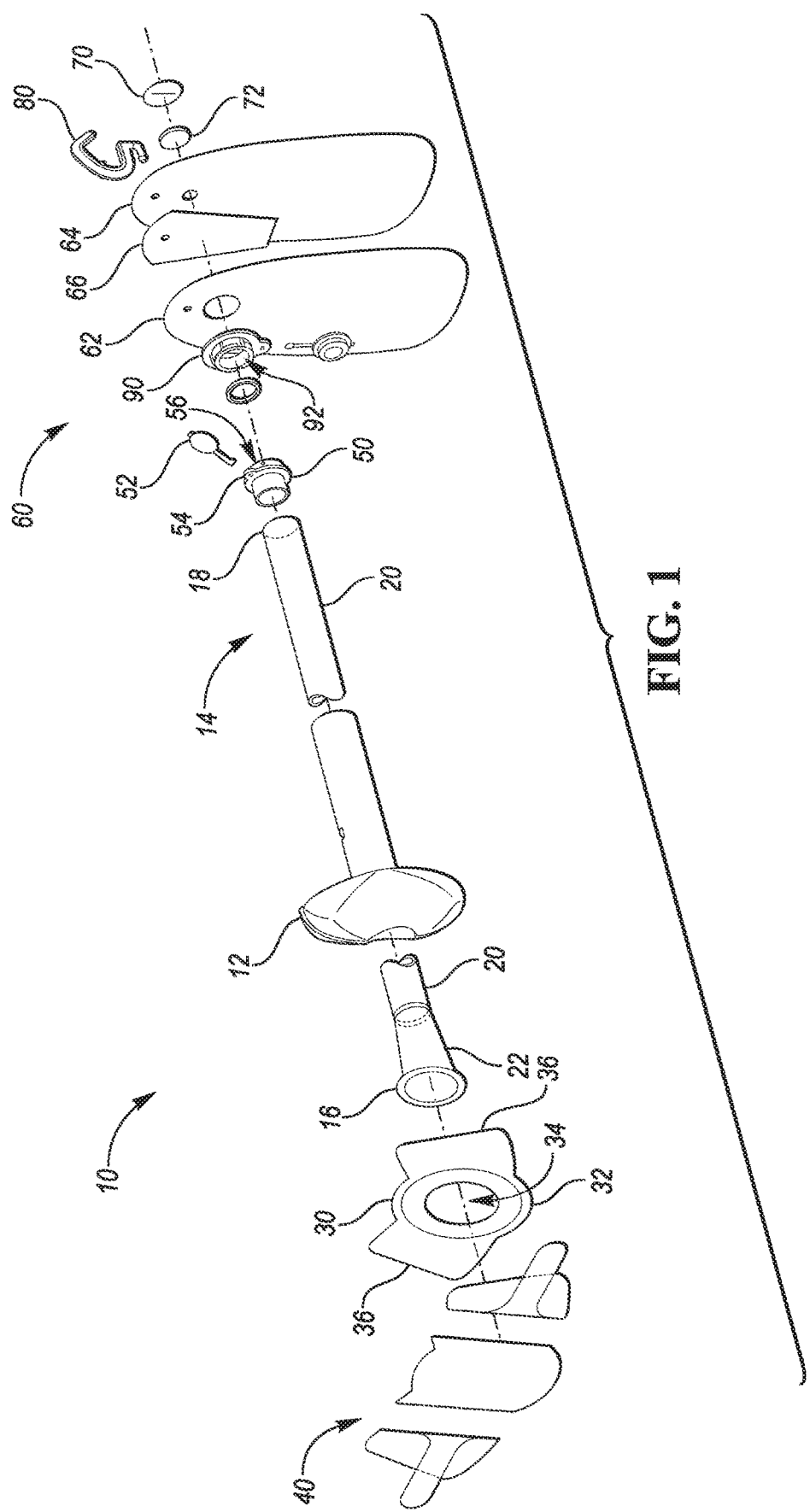
FIG. 1 is a representational view illustrating various components of a fecal management assembly.

Referring to FIG. 1, a fecal management assembly 10 includes a fecal management applicator 12 and a sheath 14 that may extend through the fecal management applicator 12. More particularly, the sheath 14 may extend through a channel of the fecal management applicator 12, as discussed in greater detail elsewhere herein.

The sheath 14 includes a first end 16 (proximal to the patient) and a second end 18 (distal from the patient). The sheath 14 may include an elongated portion 20, which may be a tubular elongated portion. The sheath 14 may further include a tapering portion 22 that extends from the elongated portion 20 to the first end 16. The tapering portion 22 may taper from a generally circular cross-section (e.g., adjacent the elongated portion 20) to a generally elliptical cross-section (e.g., adjacent the first end 16).

An adhesive substrate 30 may be affixed to the first end 16 of the sheath 14. The adhesive substrate 30 may be configured for connection to the buttocks of a patient. The adhesive substrate 30 may include a central portion 32 that defines a central aperture 34. The central aperture 34 may be an elliptical aperture that may be secured to the first end 16 of the sheath 14. The adhesive substrate 30 may further include opposing wing sections 36 that extend from the central portion 32. The adhesive substrate 30 may include, for example, a hydrocolloid adhesive disposed on a patient-interfacing side of the adhesive substrate 30. The hydrocolloid adhesive may be applied to sensitive areas of the patient's buttocks. In some approaches, the adhesive substrate 30 remains adhered to a patient for a prolonged period of time (e.g., one week or longer).

A backing layer 40 may be applied to the adhesive substrate 30. The backing layer 40 may be a single backing layer or, as shown, may include a plurality of discrete backing layer components. The backing layer 40 may be configured to protect the adhesive substrate 30 and prevent the adhesive substrate 30 from adhering prematurely or to unwanted surfaces. The backing layer 40 may comprise a material that can facilitate removal of the backing layer 40 from the adhesive substrate 30 to expose at least a portion of the adhesive substrate 30. The material may be, for example, a coated paper such as wax paper. Accordingly, the backing layer 40 may be removed from the adhesive substrate 30 prior to and/or during application of the adhesive substrate 30.

The fecal management assembly 10 may include a sheath port 50. The sheath port 50 may be provided, for example, at the second end 18 of the sheath 14. The sheath port 50 may be a discrete component separate from the sheath 14, and may be connected to the sheath 14, for example, via a clip, snap fit, heat seal, etc. Alternatively, the sheath port 50 may be integrally formed with the sheath 14 (e.g., as a single molded or extruded piece).

In some aspects, the fecal management assembly 10 may include a sheath port cap 52. The sheath port cap 52 may be tethered to the sheath port 50 (for example, at a sheath port cap connector 54), or may be tethered directly to the sheath 14. The sheath port cap 52 may be configured to mate with a sheath port opening 56 of the sheath port 50 to prevent unwanted egress of fecal matter from the sheath 14 when a collection bag is removed. The sheath port cap 52 can mate with the sheath port 50 in any suitable manner. For example, the geometry of the sheath port cap 52 can be such that the sheath port cap 52 is retained within the sheath port opening 56 of the sheath port 50 due to a tight tolerance. In this example, the sheath port cap 52 can include a portion that is sized slightly smaller than the sheath port opening 56 and/or may include pliable material that allows insertion of the sheath port cap 52 in the sheath port opening 56. Alternatively, or additionally, the sheath port cap 52 may include a mating mechanism that is complementary to the of the sheath port 50.

The fecal management assembly 10 may include a collection bag assembly 60. The collection bag assembly 60 may include a collection bag formed of a first section 62 and a second section 64. The first section 62 and the second section 64 may comprise fluid-impermeable plastic and may be affixed to one another (e.g., via heat sealing). In another approach, the collection bag is a single-component collection bag.

The collection bag assembly 60 may further include an anti-reflux device 66 that may inhibit unwanted egress of fecal matter from the collection bag assembly 60, for example, if the collection bag assembly 60 is rotated. The collection bag assembly 60 may further include a filter port 70 that allows gas to escape from the collection bag assembly 60 to prevent inflation of the collection bag assembly 60. The filter port 70 may include a filtering device 72 to diminish odor emanating from the collection bag assembly 60 via the filter port 70. A hanger 80 may be configured to allow the collection bag assembly 60 to be hung, for example, from a bed frame or a flat metal surface as is sometimes found in caregiver settings.

The collection bag assembly 60 may further include a collection bag port 90. The collection bag port 90 may be affixed to a collection bag so as to allow fecal matter to flow into the collection bag via a collection bag port opening 92.

The collection bag port 90 may be configured to mate with the sheath port 50, and vice versa. The collection bag port 90 can mate with the sheath port 50 via a connection mechanism (e.g., ball and detent, post and recess, bayonet connector, etc.) that may permit the collection bag assembly 60 to be removable secured to the sheath 14. According to one aspect, the connection mechanism is a quick connect mechanism that allows the collection bag port 90 to be quickly and easily removed from the sheath port 50. In this manner, the collection bag port 90 allows a collection bag assembly 60 to be quickly and easily removed from the sheath 14.

Because the collection bag assembly 60 may be removed from the sheath 14, portions of the fecal management assembly 10 can continue to be used after the collection bag assembly 60 is removed (e.g., while being replaced by another collection bag). As such, the sheath 14 can remain secured to the patient via the adhesive substrate 30 during replacement of the collection bag assembly 60. This may decrease discomfort and incidence of injury for the patient, as may occur during removal of the adhesive substrate 30 from the patient.

Figure 2:
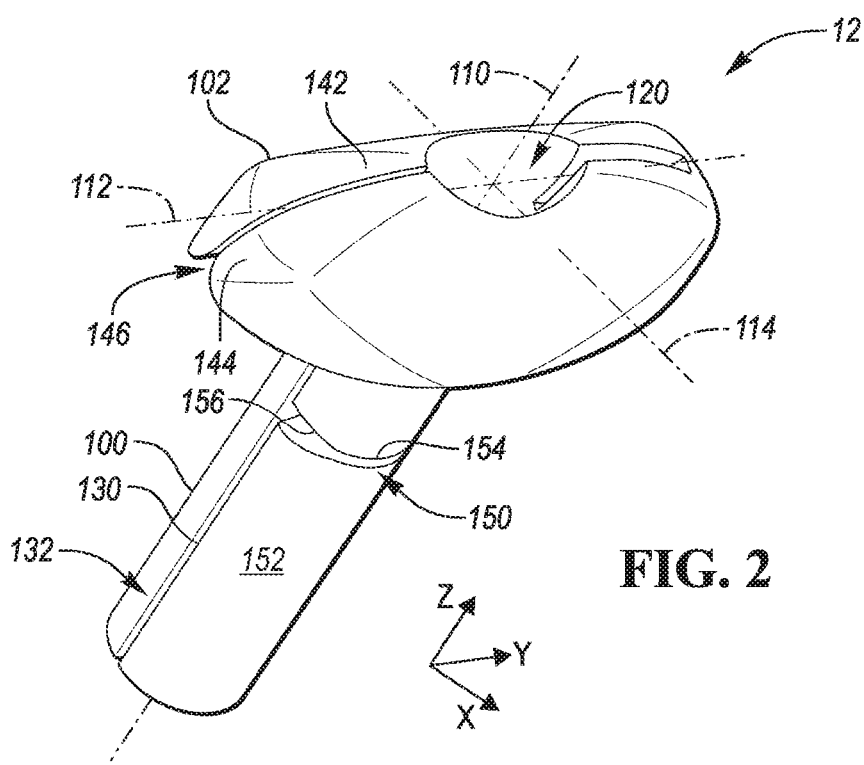
FIG. 2 is a top perspective view of a fecal management applicator.
Figure 3:
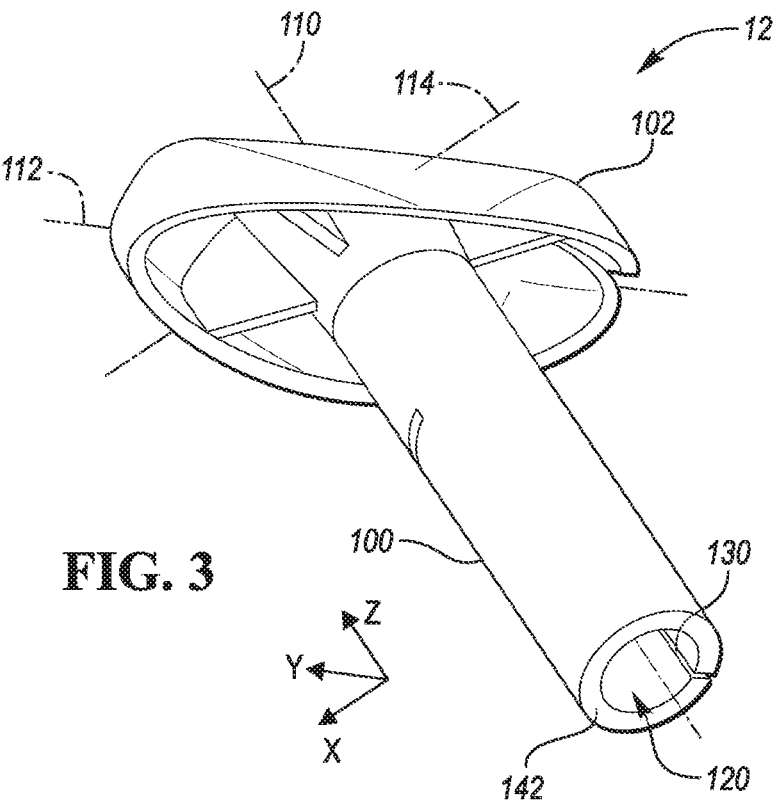
FIG. 3 is a bottom perspective view of the fecal management applicator.

Referring to FIGS. 2 and 3, the fecal management applicator 12, also referred to herein as applicator 12, includes a handle portion 100 and a head portion 102 that extends from the handle portion. At least a portion of the handle portion 100 may be in the form of an elongated tube that extends along a longitudinal axis 110, which may extend parallel to the Z axis of FIGS. 2 and 3. At least a portion of an exterior surface of the handle portion 100 may include an ergonomic hand-gripping surface. The ergonomic hand-gripping surface may be a generally smooth tubular surface, or may include other features, such as ridges, protrusions, depressions, contours, flutes, etc., that may assist a user in gripping and/or manipulating the handle portion 100.

The head portion 102 may be a generally ellipsoidal head portion having a major axis 112 that extends parallel to the Y axis, and a minor axis 114 that extends parallel to the X axis.

The applicator 12 defines a channel 120. More particularly, the handle portion 100 and the head portion 102 cooperate to define a channel 120 that extends continuously through the handle portion 100 and the head portion 102 (e.g., along the Z axis). The channel 120 may extend, for example, along an entire axial length of the applicator 12. 2. At least a portion of the channel may be a generally cylindrical channel.

The applicator 12 may include an elongated slit 130. The elongated slit 130 may be provided at a side portion of the applicator 12; for example, at side 132. The elongated slit 130 may extend through an entire thickness of the side 132 (e.g., along the Y axis direction). In this way, the elongated slit 130 may extend from the channel 120 outwardly to an external surface of the side 132. Furthermore, the elongated slit 130 may extend longitudinally (e.g., along the Z axis direction) along the entire axial length of the applicator 12. As such, the elongated slit 130 may extend through the handle portion 100 and the head portion 102. More particularly, the elongated slit 130 may extend from a bottom surface 140 of the handle portion 100 to a top surface 142 of the head portion 102.

The elongated slit 130 may extend a greater distance from the channel 120 (e.g., along the Y axis direction) in the head portion 102 as compared to in the handle portion 100. As shown in FIG. 2, the elongated slit 130 may extend from the channel 120 to a perimeter surface 144 of the head portion 102. The perimeter surface 144 may be disposed, for example, along the major axis 112 of the head portion 102. In one aspect, the perimeter surface 144 may define a tapered region 146 of the elongated slit 130.

In one aspect, the handle portion 100 may include or define a transverse slot 150. The transverse slot 150 may be provided at a forward-facing wall 152 of the handle portion 100. The forward-facing wall 152 may be angularly offset (e.g., about the longitudinal axis 110) from the side 132 of the handle portion 100. The transverse slot 150 may extend through an entire thickness of the forward-facing wall 152 (e.g., along the X axis direction from the channel 120 to an exterior surface of the forward-facing wall 152).

Figure 4:
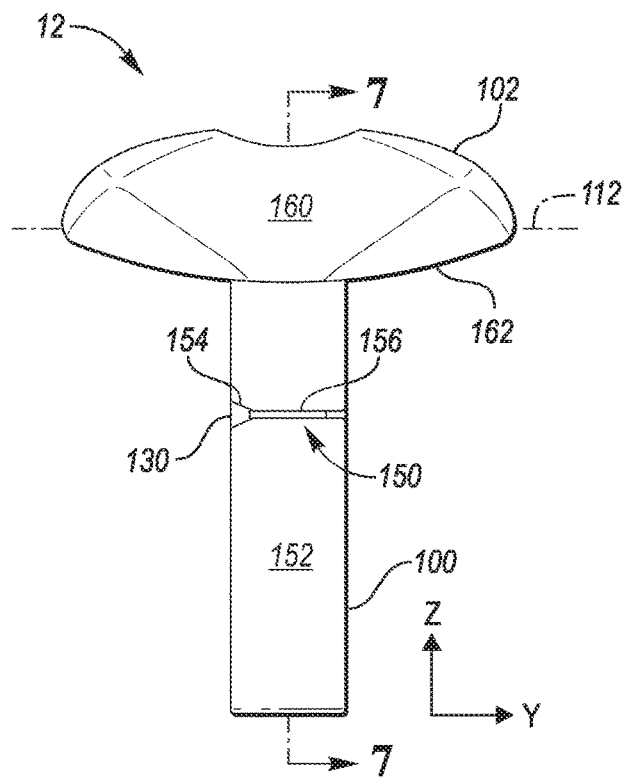
FIG. 4 is a front elevation view of the fecal management applicator.
Figure 5:
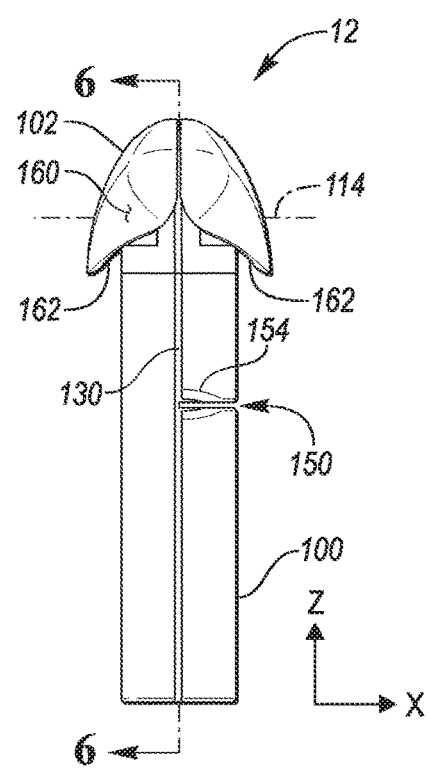
FIG. 5 is a side elevation view of the fecal management applicator.

Referring to FIGS. 4 and 5, the transverse slot 150 may extend from the elongated slit 130, and may extend in a plane defined by the X and Y axes. In one aspect, the transverse slot includes a tapered region 154 that extends from the elongated slit 130, and a constant-width, or substantially constant-width, region 156 that extends from the tapered region 154.

The head portion 102 may include an outer surface 160. The outer surface 160 may include the perimeter surface 144, previously discussed. The outer surface 160 may be a generally ellipsoidal outer surface. As such, the outer surface 160 may have a first slope in a direction of the major axis 112 that is more gradual than a second slope in a direction of the minor axis 114. A lower edge 162 of the head portion 102 may generally define a hyperbolic paraboloid.

Figure 6:
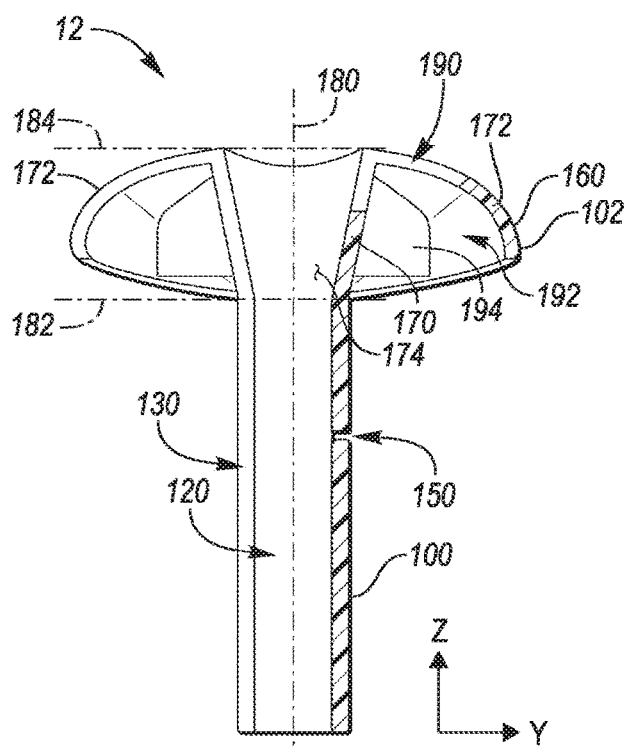
FIG. 6 is a cross-sectional view taken along line 6-6 of FIG. 5.
Figure 7:
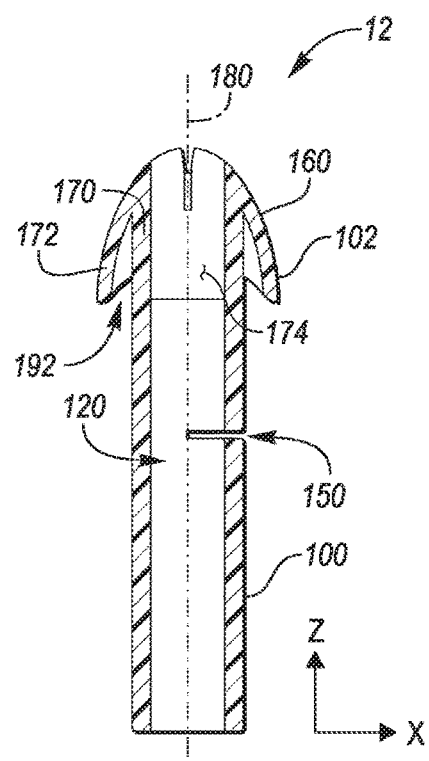
FIG. 7 is a cross-sectional view taken along line 7-7 of FIG. 4.

Referring to FIGS. 6 and 7, the head portion 102 may include an inner head wall portion 170 and an outer head wall portion 172. The inner head wall portion 170 may extend axially (e.g., in the Z direction) from the handle portion 100. The outer head wall portion 172 may extend from the inner head wall portion 170. For example, the outer head wall portion 172 may extend radially outwardly from the inner head wall portion 170 (e.g., generally in the Y direction). The outer head wall portion 172 may also curve over the inner head wall portion 170 (e.g., generally outwardly in the Y direction and downwardly in the Z direction). The outer head wall portion 172 may define at least a portion of the outer surface 160 and at least a portion of the lower edge 162.

Figure 8:
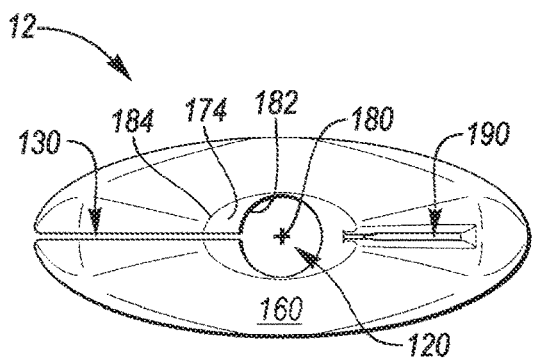
FIG. 8 is a top plan view of the fecal management applicator.

Referring to FIGS. 6-8, at least a portion of the inner head wall portion 170 may be tapered relative to a central axis 180 of the channel 120. More particularly, an inner surface 174 of the inner head wall portion 170 may taper outwardly (e.g., in the Y direction) as the inner surface 174 of the inner head wall portion 170 extends away from the handle portion 100 (e.g., in the Z direction). In one aspect, the inner head wall portion 170 tapers outwardly in a first vertical cross-sectional plane, such as the Y-Z plane of FIG. 6, and is substantially parallel in a second vertical cross-sectional plane that is transverse to the first vertical cross-sectional plane, such as the X-Z plane of FIG. 7. Furthermore, the inner head wall portion 170 may have a generally circular shape at a first axial height 182 along the central axis 180, and may have a generally elliptical shape at a second axial height 184 that is axially offset from the first axial height.

The head portion 102 may include or define a head slot 190. The head slot 190 may extend through at least one of the inner head wall portion 170 and the outer head wall portion 172. The head slot 190 may extend from the channel 120 opposite the elongated slit 130 (e.g., generally parallel to the Y axis). In one aspect, at least a portion of the head slot 190 may have a thickness (e.g., in the X direction) that is greater than a thickness of the elongated slit 130. For example, the head slot 190 may have a thickness that is approximately (e.g., +/−10%) 1 mm greater than the thickness of the elongated slit 130.

Figure 9:
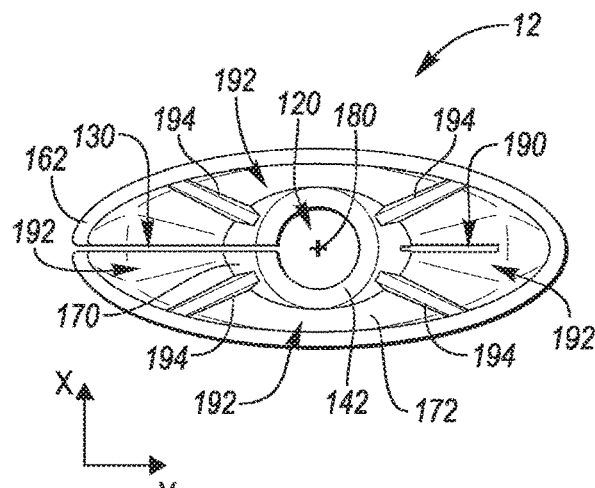
FIG. 9 is a bottom plan view of the fecal management applicator.

Referring to FIG. 9, the head portion 102 may include one or more gaps 192 between the outer head wall portion 172 and the inner head wall portion 170. In this way, at least a portion of the outer head wall portion 172 may be spaced apart from at least a portion of the inner head wall portion 170. More particularly, a radially-inward surface of the outer head wall portion 172 may be spaced apart from a radially-outward surface of the inner head wall portion 170.

The head portion 102 may include one or more ribs 194 that extend from the inner head wall portion 170 to the outer head wall portion 172. The ribs 194 may be reinforcing ribs that provide support for the outer head wall portion 172.

Figure 10:
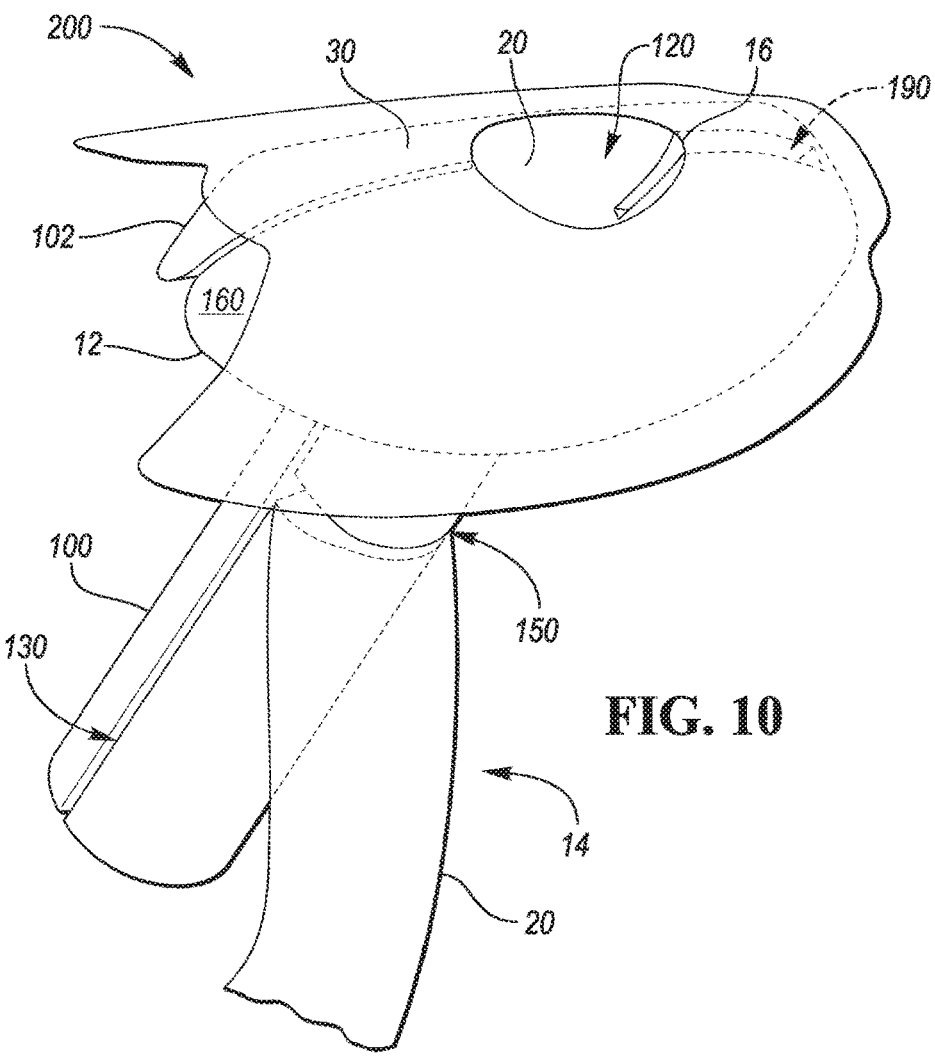
FIG. 10 is a perspective view of a portion of the fecal management assembly FIG. 1 in an assembled configuration.

Referring to FIG. 10, a portion 200 of the fecal management assembly 10 of FIG. 1 is shown in an assembled configuration. More particularly, the sheath 14 is shown with the adhesive substrate 30 attached thereto (e.g., at the first end 16 of the tapering portion 22 of the sheath 14). The sheath 14 and adhesive substrate 30 are assembled with the applicator 12.

A method of assembling the portion 200 may include inserting the sheath 14 through the elongated slit 130 of the applicator 12 and into the channel 120. Inserting the sheath 14 may include disposing at least a portion of the tapering portion 22 of the sheath 14 within the head portion 102 of the applicator 12, and disposing at least a portion of the elongated portion 20 within the handle portion 100. The method may include placing the adhesive substrate across at least a portion of the outer surface 160 of the head portion 102. The method may further include placing at least a portion of the sheath 14 (e.g., the elongated portion 20 of the sheath 14) through the transverse slot 150 of the handle portion 100. This may allow a user to adjust a tension of the sheath 14 within the channel 120 and/or the tension of the adhesive substrate 30 across the outer surface 160.

A method of assembling the fecal management assembly 10 may include connecting the sheath 14 to a collection bag assembly (e.g., the collection bag assembly 60 of FIG. 1). Upon connecting, a collection bag may be provided in fluidic communication with the second end of the sheath 14.

A method of applying the fecal management assembly 10 may include applying the adhesive substrate 30, via the applicator 12, to a patient (e.g., to a patient's buttocks proximate the patient's anus). Applying the adhesive substrate 30 to the patient may secure adhesive of the adhesive substrate 30 to the patient. The method may further include manipulating the handle portion 100 of the applicator 12 to rotate portions of the head portion 102 (and thereby, the adhesive substrate 30) toward and away from the patient's skin. Such manipulation may achieve a fluid-tight (or substantially fluid-tight) seal between the adhesive substrate 30 and the patient's skin.

A method of removing the applicator 12 may include removing a portion of the sheath 14 from the transverse slot 150 of the handle portion 100. The method may further include removing the sheath 14 from the channel 120 of the applicator 12. Removal of the sheath 14 from the channel 120 may include passing the sheath 14 through the elongated slit 130 of the applicator 12.

As such, the applicator 12 may be provided to assist a user in applying an adhesive substrate 30 to a patient. Upon application of the adhesive substrate 30, the applicator 12 may be removed from the sheath 14, while the sheath 14 remains secured to the patient via the adhesive substrate 30. The applicator 12 may subsequently be discarded, or may be cleansed or decontaminated (e.g., disinfected or sterilized) for future use.

Figure 11:
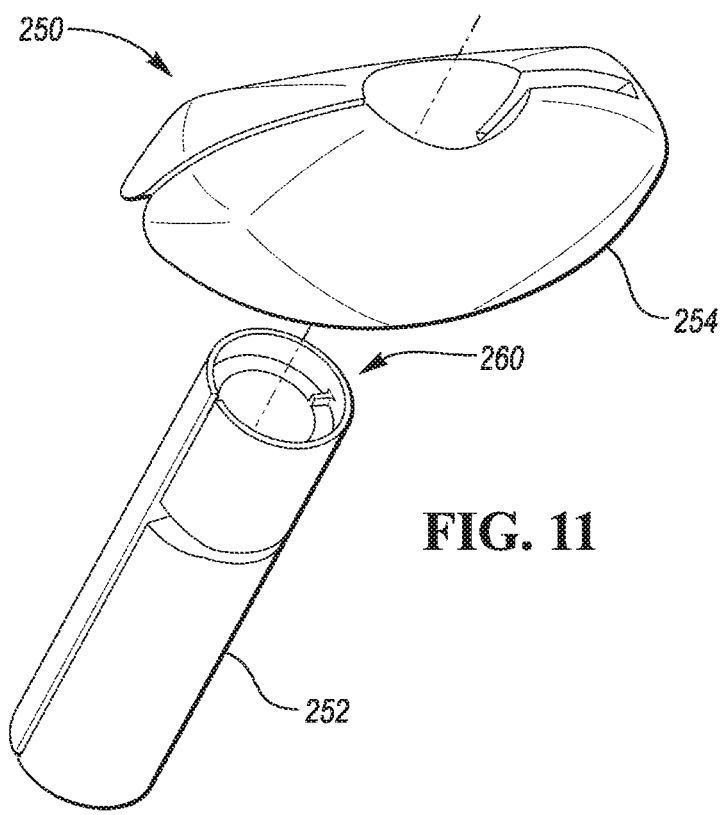
FIG. 11 is a first exploded perspective view of another fecal management applicator.
Figure 12:
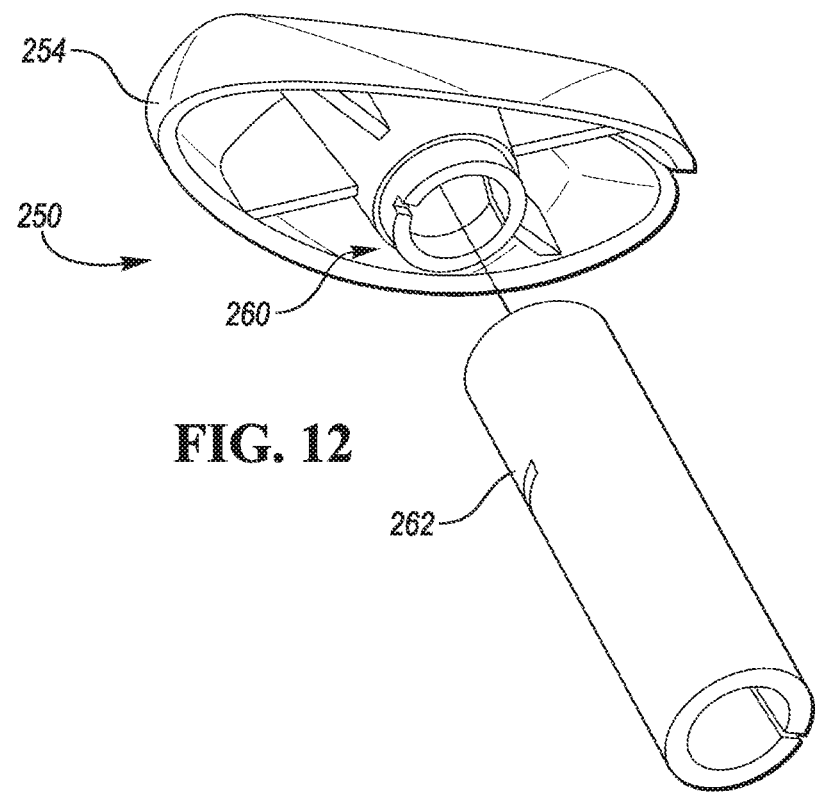
FIG. 12 is a second exploded perspective view of the fecal management applicator of FIG. 11.

Referring to FIG. 11, a fecal management applicator, referred to herein as applicator 250, is shown. The applicator 250 may include a handle body 252 and a head body 254. The handle body 252 may generally correspond to handle portion 100, previously discussed. Similarly, the head body 254 may generally correspond to head portion 102, previously discussed.

In the approach of FIG. 11, the handle body 252 and the head body 254 may be discretely formed bodies. That is, the handle body 252 and the head body 254 are formed as separate components.

The handle body 252 may be formed at least in part of a material having a first hardness, and the head body 254 may be formed at least in part of a material having a second hardness that is different than the first hardness. More particularly, the handle body 252 may have a greater hardness than the hardness of the head body 254. Each hardness may be measured, for example, with a durometer, and may be express on a durometer scale such as the Shore A or Shore D scale.

In one aspect, the handle body 252 may be formed at least in part of a first material, and the head body 254 may be formed at least in part of a second material that is different than the first material. In another aspect, the handle body 252 and the head body 254 are formed at least in part of a common material, such that the common material has a first hardness in the handle body 252 and a second hardness in the head body 254 that is different than the first hardness.

The handle body 252 may have a first interface 260, and the head body 254 may have a second interface 262 for interfacing the first interface 260. The first interface 260 and the second interface 262 may have complementary geometries (e.g., complementary protrusions and receptacles). During assembly, the first interface 260 of the handle body 252 may be brought into engagement with the second interface 262 of the head body 254. The head body 254 may be fixedly secured to the handle body 252. For example, the head body 254 may be bonded to the handle body 252 with an adhesive or by a welding process (e.g., ultrasonic welding).

As such, in the assembled configuration, the applicator 250 may have a relatively rigid handle body 252, and a relatively flexible head body 254. The relatively rigid handle body 252 may assist a user in manipulating the applicator 250, while the relatively flexible head body 254 may assist in applying and/or securing an adhesive substrate (e.g., adhesive substrate 30) to a patient. Also in the assembled configuration, the applicator 250 may include one or more features of the applicator 12, previously discussed. As such, the applicator 250 in the assembled configuration may generally correspond to the applicator 12.

Figure 13:
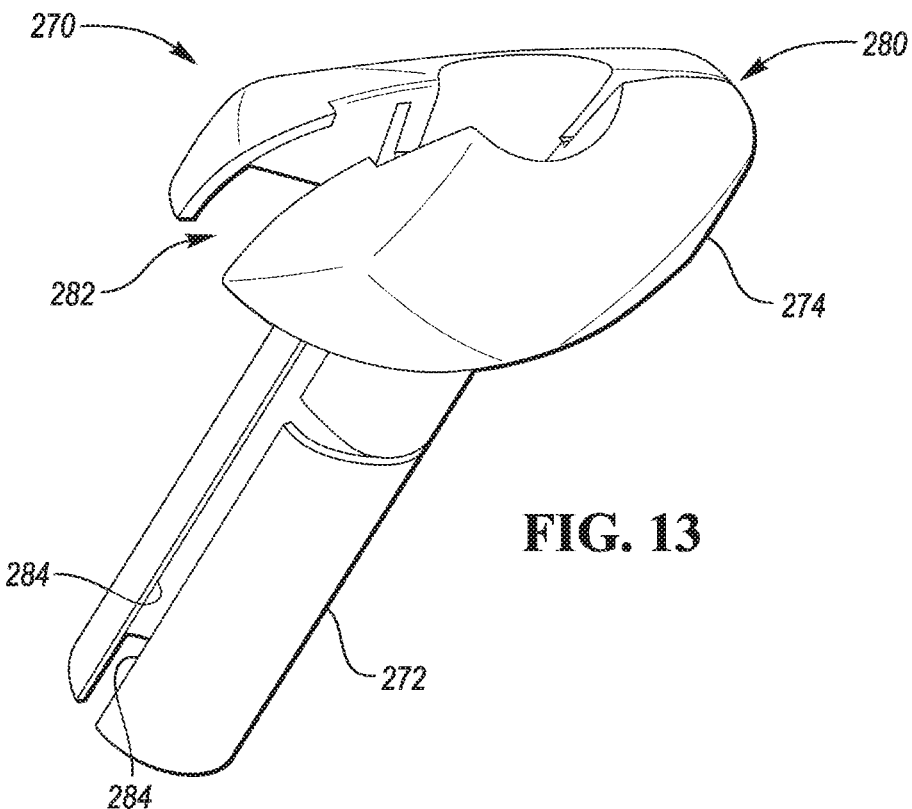
FIG. 13 is a first perspective view of another fecal management applicator.
Figure 14:
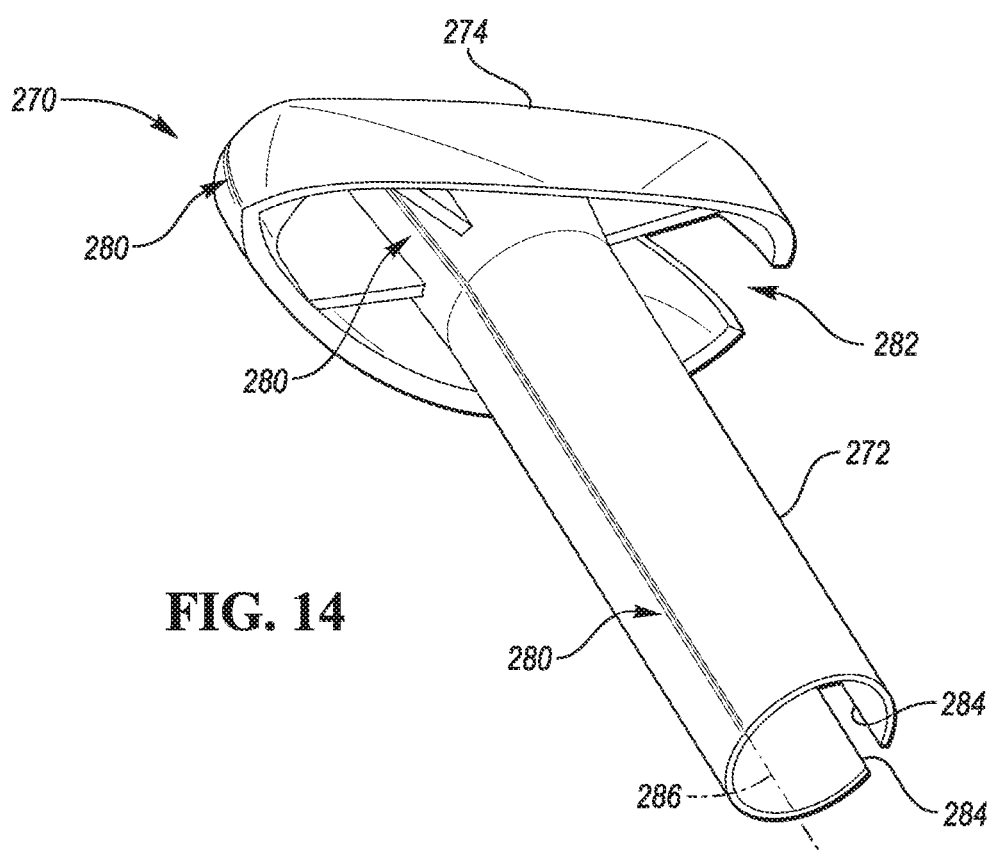
FIG. 14 is a second perspective view of the fecal management applicator of FIG. 13.
Figure 15:
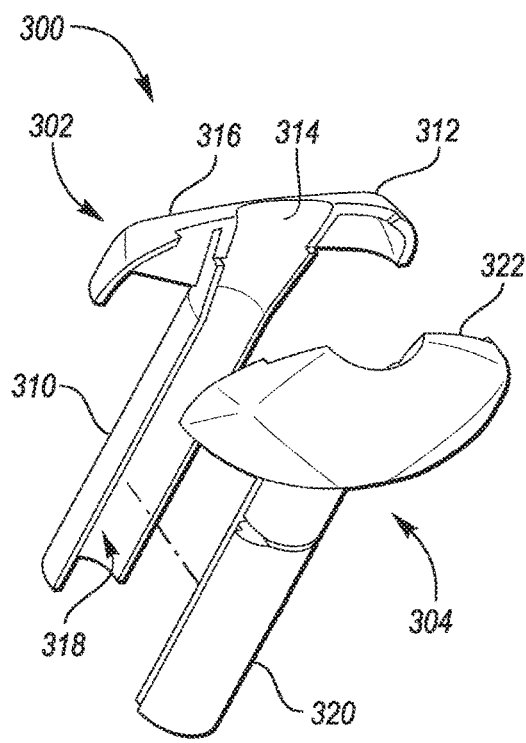
FIG. 15 is a first perspective view of another fecal management applicator in an open configuration.
Figure 16:
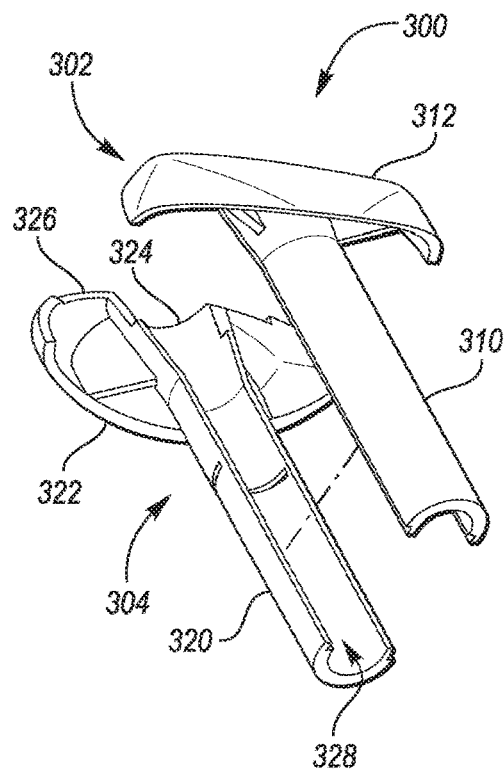
FIG. 16 is a second perspective view of the fecal management applicator of FIG. 15 in the open configuration.

Referring to FIGS. 13 and 14, a fecal management applicator, referred to herein as applicator 270, is shown. The applicator may include a handle portion 272 and a head portion 274. The applicator 270 may include one or more features that generally correspond to applicator 12, previously discussed. For example, the handle portion 272 may generally correspond to handle portion 100, and the head portion 274 may generally correspond to head portion 102.

The applicator 270 may include a hinge region 280, and an expandable elongated slit 282 disposed opposite (e.g., diametrically opposite) the hinge region 280. As shown in FIG. 14, the hinge region 280 may extend through at least a portion of the handle portion 272. The hinge region 280 may also, or may instead, extend through at least a portion of the head portion 274.

The hinge region 280 may permit slit edges 284 of the expandable elongated slit 282 to expand apart. For example, the slit edges 284 may rotate about a hinge axis 286, as shown in FIG. 14. In at least one approach, the hinge region 280 includes a living hinge. As such, a material thickness of one or both of the handle portion 272 and the head portion 274 may be reduced at the hinge region 280. The applicator 270 may be configured to bias the expandable elongated slit 282 toward a closed configuration, and the living hinge may be adapted to permit expansion of the slit edges 284 of the expandable elongated slit 282. In at least another approach, a hinge pin is provided at the hinge region 280 to permit relative rotation of the slit edges 284 about the hinge axis 286.

Referring to FIGS. 15-18, a fecal management applicator, referred to herein as applicator 300, is shown. The applicator 300 may include a first side member 302 and a second side member 304.

The first side member 302 may include a first handle portion 310 and a first head portion 312. The first head portion 312 may include a first inner wall portion 314 that extends from the first handle portion 310, and a first outer wall portion 316 that extends radially outwardly from the first inner wall portion 314. The first outer wall portion 316 may also curve over the first inner wall portion 314. The first side member 302 may include a first channel portion 318 that may extend along the first handle portion 310 and the first head portion 312 (e.g., along the first inner wall portion 314).

The second side member 304 may include a second handle portion 320 and a second head portion 322. The second head portion 322 may include a second inner wall portion 324 that extends from the second handle portion 320, and a second outer wall portion 326 that extends radially outwardly from the second inner wall portion 324. The second outer wall portion 326 may also curve over the second inner wall portion 324. The second side member 304 may include a second channel portion 328 that may extend along the second handle portion 320 and the second head portion 322 (e.g., along the second inner wall portion 324).

The first side member 302 may include a first connection interface 330, and the second side member 304 may include a second connection interface 332. In one aspect, one or both of the first connection interface 330 and the second connection interface 332 may include an interference-fit interface, press-fit interface, friction-fit interface, or the like. As such, the first connection interface 330 and the second connection interface 332 may have complementary geometries (e.g., complementary ridges, protrusions, receptacles, etc.). The first connection interface 330 may be configured to engage the second connection interface 332 (or vice versa) to secure the first side member 302 to the second side member 304.

Figure 17:
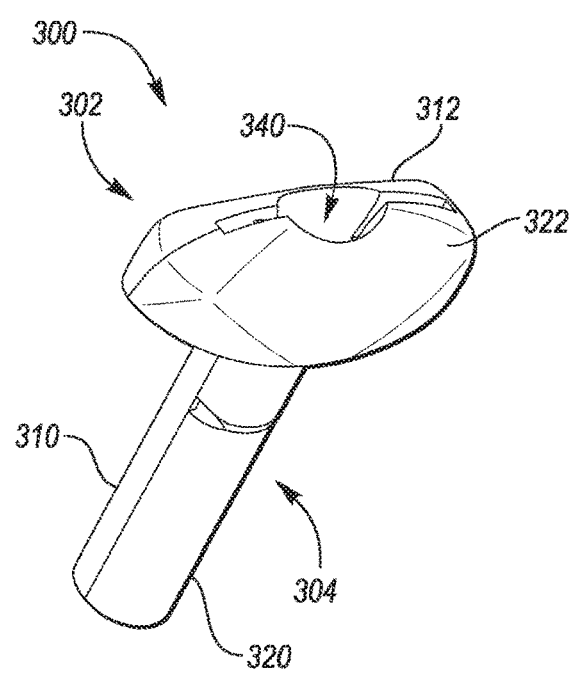
FIG. 17 is a first perspective view of the fecal management applicator of FIG. 15 in a closed configuration.
Figure 18:
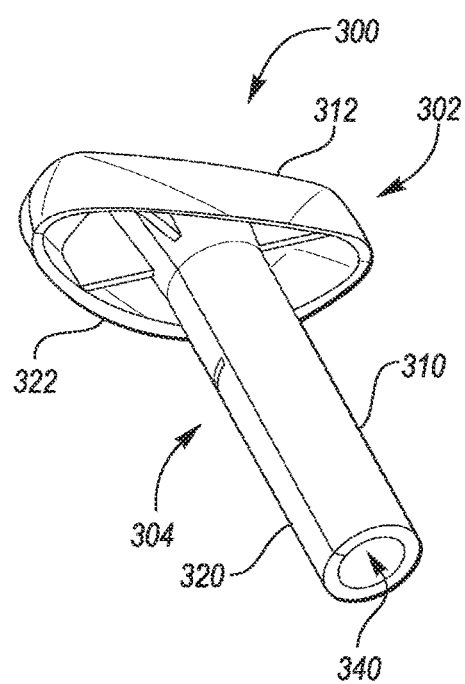
FIG. 18 is a second perspective view of the fecal management applicator of FIG. 15 in the closed configuration.

In an assembled configuration, shown in FIGS. 17 and 18, the first side member 302 and the second side member 304 may be disposed in engagement to form the assembled applicator 300. The engagement may be a releasable engagement such that the second side member 304 may be selectively disengaged from the first side member 302.

Also in the assembled configuration, the applicator 300 may include one or more features of the applicator 12, previously discussed. For example, the first side member 302 and the second side member 304 may cooperate to define a channel 340 therebetween. More particularly, the first channel portion 318 and the second channel portion 328 may cooperate to define the channel 340 therebetween. The channel 340 may extend continuously through along an entire axial length of the assembled applicator. As such, the applicator 300 in the assembled configuration may generally correspond to the applicator 12.

The various components and features discussed with respect to an individual applicator 12, 250, 270, 300 discussed herein may be used interchangeably with the fecal management assembly 10 of FIG. 1 and/or the portion 200 of the fecal management assembly 10 discussed with respect to FIG. 10.

Furthermore, the various components and features discussed with respect to an individual applicator 12, 250, 270, 300 discussed herein are not limited to such applicator. As such, it is expressly contemplated that various components and features of an individual applicator 12, 250, 270, 300 may be provided with, or incorporated into, other applicators discussed herein.

While exemplary embodiments are described above, it is not intended that these embodiments describe all possible forms encompassed by the claims. The words used in the specification are words of description rather than limitation, and it is understood that various changes may be made without departing from the spirit and scope of the disclosure. As previously described, the features of various embodiments may be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics may be compromised to achieve desired overall system attributes, which depend on the specific application and implementation. These attributes may include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and may be desirable for particular applications.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A fecal management applicator comprising:
a handle portion; and
a head portion extending from the handle portion, the head portion including an inner head wall portion that extends axially from the handle portion and defines at least a portion of a channel, and an outer head wall portion that extends radially outwardly from the inner head wall portion and curves over the inner head wall portion, wherein the channel extends continuously through the handle portion and the head portion along an entire axial length of the fecal management applicator, wherein at least a portion of the inner head wall portion tapers outwardly relative to a central axis of the channel to form an outwardly tapering channel portion.

2. The fecal management applicator of claim 1 wherein a channel-facing portion of the inner head wall portion tapers outwardly in first vertical cross-sectional plane, and wherein the channel-facing portion of the inner head wall portion is substantially parallel in a second vertical cross-sectional plane that is transverse to the first vertical cross-sectional plane.

3. The fecal management applicator of claim 1 wherein the inner head wall portion has a generally circular shape at a first axial height, and has a generally elliptical shape at a second axial height that is axially offset from the first axial height.

4. The fecal management applicator of claim 3 wherein the outer head wall portion is generally ellipsoidal.

5. The fecal management applicator of claim 4 wherein the generally ellipsoidal outer head wall portion has a first slope in a direction of a major axis that is more gradual than a second slope in a direction of a minor axis.

6. The fecal management applicator of claim 1 wherein the head portion defines a gap defining a hollow space between the outer head wall portion and the inner head wall portion such that at least a portion of the outer head wall portion is spaced apart from at least a portion of the inner head wall portion.

7. The fecal management applicator of claim 6 wherein the head portion includes at least one rib extending within the gap from the inner head wall portion to the outer head wall portion.

8. The fecal management applicator of claim 1 wherein the handle portion is a handle body having a first material hardness, and wherein the head portion is a head body having a second material hardness different than the first material hardness.

9. A fecal management applicator comprising:
a handle portion; and
a head portion extending from the handle portion, the head portion including an inner head wall portion that extends axially from the handle portion and an outer head wall portion that extends radially outwardly from the inner head wall portion and curves over the inner head wall portion, wherein the fecal management applicator defines a channel that extends continuously through the handle portion and the head portion along an entire axial length of the fecal management applicator, wherein the fecal management applicator defines an elongated slit that extends axially through a side of the fecal management applicator along the entire axial length of the fecal management applicator.

10. The fecal management applicator of claim 9 wherein the elongated slit extends from the channel and through a perimeter surface of the head portion.

11. The fecal management applicator of claim 10 wherein the head portion defines a head slot extending through at least one of the inner head wall portion and the outer head wall portion, the head slot extending from the channel opposite the elongated slit.

12. The fecal management applicator of claim 9 wherein the handle portion defines a transverse slot extending from the elongated slit.

13. The fecal management applicator of claim 12 wherein the transverse slot includes a tapered slot region that extends from the elongated slit.

14. The fecal management applicator of claim 9 wherein the fecal management applicator includes a hinge region disposed diametrically opposite from the elongated slit.

15. The fecal management applicator of claim 14 wherein the hinge region includes a living hinge configured to bias the elongated slit toward a closed configuration, and adapted to permit expansion of the fecal management applicator at the elongated slit.

16. The fecal management applicator of claim 1 wherein the inner head wall portion forms a frustoconical channel portion.

17. The fecal management applicator of claim 9 wherein a head portion of the elongated slit is circumferentially aligned with a handle portion of the elongated slit.

18. The fecal management applicator of claim 9 wherein handle portion is closed diametrically opposite the elongated slit.

19. The fecal management applicator of claim 9 wherein the head portion defines a head slot extending through each of the inner head wall portion and the outer head wall portion.

20. The fecal management applicator of claim 9 wherein the head portion defines a head slot that extends from an upper surface of the head portion downwardly through less than an entire axial depth of the head portion.

21. The fecal management applicator of claim 12 wherein the transverse slot extends orthogonally from the elongated slit.

22. The fecal management applicator of claim 12 wherein the transverse slot includes a tapered slot region at a transverse intersection with the elongated slit.

* * * * *